(12) United States Patent
Nishijima (10) Patent No.: US 9,714,913 B2
(45) Date of Patent: Jul. 25, 2017

(54) CONTROL DEVICE FOR EXHAUST GAS SENSOR

(75) Inventor: Hiroki Nishijima, Suntou-gun (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 164 days.

(21) Appl. No.: 14/356,431

(22) PCT Filed: Feb. 14, 2012

(86) PCT No.: PCT/JP2012/053381
§ 371 (c)(1),
(2), (4) Date: May 6, 2014

(87) PCT Pub. No.: WO2013/121524
PCT Pub. Date: Aug. 22, 2013

(65) Prior Publication Data
US 2014/0346041 A1    Nov. 27, 2014

(51) Int. Cl.
*G01N 27/407* (2006.01)
*G01N 27/406* (2006.01)
(Continued)

(52) U.S. Cl.
CPC ......... *G01N 27/407* (2013.01); *F02D 41/123* (2013.01); *F02D 41/146* (2013.01);
(Continued)

(58) Field of Classification Search
CPC .................................................. F02D 41/1441
See application file for complete search history.

(56) References Cited

U.S. PATENT DOCUMENTS 5,845,489 A * 12/1998 Dohta .................... F01N 11/00
123/688
6,286,493 B1    9/2001 Aoki
(Continued)

FOREIGN PATENT DOCUMENTS

JP       08-128979 A      5/1996
JP    2000-258387 A      9/2000
(Continued)

OTHER PUBLICATIONS

International Search Report of PCT/JP2012/053381 dated Apr. 24, 2012.

*Primary Examiner* — Sean E Conley
*Assistant Examiner* — Matthew Krcha
(74) *Attorney, Agent, or Firm* — Sughrue Mion, PLLC (57) ABSTRACT

A control device for an exhaust gas sensor includes first means for estimating a temperature of a sensor element in accordance with impedance of a solid electrolyte, and second means for estimating the temperature of the sensor element in accordance with resistance of a heater. A first element temperature according to impedance of the sensor element in a predetermined detection timing is detected by the first means, and a second element temperature according to resistance of a heater of the sensor element in the predetermined detection timing is detected by the second means. The control device corrects the temperature of the sensor element that is estimated in accordance with heater resistance by the second means in accordance with a difference between the first element temperature and the second element temperature.

10 Claims, 7 Drawing Sheets

(51) Int. Cl.
  *F02D 41/14*   (2006.01)
  *F02D 41/22*   (2006.01)
  *F02D 41/12*   (2006.01)

(52) U.S. Cl.
  CPC ..... *F02D 41/1441* (2013.01); *F02D 41/1494* (2013.01); *F02D 41/222* (2013.01); *G01N 27/4067* (2013.01); *F02D 2200/0804* (2013.01)

(56) References Cited

U.S. PATENT DOCUMENTS

| | | | |
|---|---|---|---|
| 2004/0047396 A1* | 3/2004 | Nomura | G01N 27/4067 374/141 |
| 2006/0117737 A1 | 6/2006 | Ohsaki | |
| 2009/0071951 A1 | 3/2009 | Suzuki | |
| 2009/0308135 A1 | 12/2009 | Reinshagen et al. | |

FOREIGN PATENT DOCUMENTS

| | | | |
|---|---|---|---|
| JP | 2003-270194 A | 9/2003 |
| JP | 2004-069547 A | 3/2004 |
| JP | 2006-161625 A | 6/2006 |
| JP | 2006-214885 A | 8/2006 |
| JP | 2009-014652 A | 1/2009 |
| JP | 2009-053108 A | 3/2009 |
| JP | 2009-266743 A | 11/2009 |
| WO | 2006077711 A1 | 7/2006 |
| WO | 2007/099647 A1 | 9/2007 |

* cited by examiner

S102: PRECONDITIONS ARE ESTABLISHED?
S104: DETECT IMPEDANCE AND Ro
S106: CALCULATE |Ti0-Tr0|
S110: SENSOR IS DETERMINED AS ABNOMAL
S112: SENDOR IS DETERMINED AS NOMAL
S116: CORRECT RELATION OF R AND Tr

CONTROL DEVICE FOR EXHAUST GAS SENSOR

CROSS REFERENCE TO RELATED APPLICATIONS

This is a National Stage of International Application No. PCT/JP2012/053381 filed Feb. 14, 2014, the content of all of which is incorporated herein by reference in its entirety.

TECHNICAL FIELD

The present invention relates to a control device for an exhaust gas sensor. More specifically, the invention relates to a control device for an exhaust gas sensor including a pair of electrodes disposed at both sides of a solid electrolyte, and a heater.

BACKGROUND ART

A system that detects an air-fuel ratio, an NOx concentration and the like of exhaust gas by using an exhaust gas sensor including a pair of electrodes disposed at both sides of a solid electrolyte is generally known. In order to ensure high detection precision in the system like this, it is important to control the temperature of the sensor element (the element temperature) of an exhaust gas sensor to an appropriate temperature. For example, Patent Literature 1 discloses the system that controls the temperature of the air-fuel ratio sensor disposed in the exhaust channel of an internal combustion engine in accordance with the impedance of a solid electrolyte.

CITATION LIST

Patent Literature

Patent Literature 1: Japanese Patent Laid-Open No. 2009-053108
Patent Literature 2: Japanese Patent Laid-Open No. 2006-161625
Patent Literature 3: Japanese Patent Laid-Open No. 08-128979
Patent Literature 4: Japanese Patent Laid-Open No. 2009-266743
Patent Literature 5: Japanese Patent Laid-Open No. 2009-014652
Patent Literature 6: Japanese Patent Laid-Open No. 2003-270194
Patent Literature 7: Japanese Patent Laid-Open No. 2004-069547
Patent Literature 8: Japanese Patent Laid-Open No. 2000-258387
Patent Literature 9: Japanese Patent Laid-Open No. 2006-214885

SUMMARY OF INVENTION

Technical Problem

The impedance of the solid electrolyte disposed between a pair of electrodes of an exhaust gas sensor and the element temperature show a stable correlation in a temperature region that is high to some extent. Accordingly, when the exhaust gas sensor functions normally, and the temperature of the sensor element is increased, a temperature can be detected accurately to some extent based on the impedance of the solid electrolyte.

However, the correlation between the impedance of the solid electrolyte and the element temperature is not stabilized in the state at a low temperature, and variation sometimes arises in the element temperature that is detected in accordance with the impedance in a low temperature region. Further, due to deterioration of an exhaust gas sensor, a deviation sometimes occurs to the relation between the impedance and the element temperature. In this case, it is conceivable that the element temperature that is estimated in accordance with the impedance deviates from the actual element temperature, and affects the control using the exhaust gas sensor.

Further, there is also a correlation between heater resistance and an element temperature. Accordingly, by detecting the resistance of a heater, the element temperature can be estimated in accordance with the resistance. However, it is conceivable when the heater resistance changes due to secular deterioration or the like of the heater, a deviation occurs between the element temperature that is estimated and the actual element temperature.

Accordingly, such a system is desired that accurately detects the temperature of the exhaust gas sensor even when the element temperature is low, and can detect abnormality of the exhaust gas sensor when the exhaust gas sensor is in a state in which detection precision of the element temperature cannot be compensated.

The present invention has an object to solve the above described problems, and provides a control device for an exhaust gas sensor that is improved to detect presence or absence of abnormality of an exhaust gas sensor, and to be able to enhance detection precision of the element temperature of the exhaust gas sensor.

Solution to Problem

In order to attain the above described object, the present invention is a control device for an exhaust gas sensor, and the exhaust gas sensor is disposed in an exhaust channel of an internal combustion engine, and includes a solid electrolyte, a pair of electrodes disposed with the solid electrolyte therebetween, and a heater that heats a sensor element of the exhaust gas sensor. The control device for the exhaust gas sensor of the present invention includes first means for estimating a temperature of the sensor element in accordance with impedance of the solid electrolyte, and second means for estimating the temperature of the sensor element in accordance with resistance of the heater. The control device further includes correction means for correcting the temperature of the sensor element that is estimated by the second means, in accordance with a difference between a first element temperature and a second element temperature. Here, the first element temperature is the temperature of the sensor element that is estimated by the first means in accordance with the impedance detected at a predetermined detection timing. The second element temperature is the temperature of the sensor element that is estimated by the second means in accordance with the resistance of the heater that is detected at a timing corresponding to the predetermined detection timing. Note that "timing corresponding to the predetermined detection timing" for detecting the heater resistance includes a timing that is practically simultaneous with the predetermined detection timing. Namely, the timing for detecting the heater resistance may be simultaneous with the predetermined timing, and, for example, when a response delay or the like arises between detection of impedance and detection of the heater, the timing for detecting the heater resistance may be a timing with the delay taken into consideration.

Further, in the control device for an exhaust gas sensor of the present invention, the second means may estimate the temperature of the sensor element based on a relation of the resistance of the heater and the temperature of the sensor element. In this case, the correction means corrects the relation of the resistance of the heater and the temperature of the sensor element in accordance with the difference between the first element temperature and the second element temperature, and thereby corrects the temperature of the sensor element by the second means.

In the present invention, the predetermined detection timing can be set as a timing in a time period in which the temperature of the sensor element is higher than the reference temperature.

Alternatively, in the present invention, the predetermined detection timing may be set as a timing during a fuel cut operation of the internal combustion engine, or during stoppage in idle stop control of the internal combustion engine, or in a time period of an operation state of the internal combustion engine in which an addition amount of an aqueous urea solution from an aqueous urea solution adding valve of a urea SCR system that is installed in the exhaust channel is smaller than a reference addition amount.

The control device for an exhaust gas sensor of the present invention may further include means for performing heater ON/OFF control that alternately realizes a state in which power is supplied to the heater, and a state in which power supply is stopped. In this case, the predetermined detection timing may be set as a timing during the heater ON/OFF control.

Further, the control device for an exhaust gas sensor of the present invention may further include means for setting an upper limit temperature that is an upper limit value of the temperature of the sensor element in accordance with an outside air temperature or an exhaust gas temperature or a temperature of cooling water of the internal combustion engine, during stoppage of an operation of the internal combustion engine, and means for performing power control that escalates supply power to the heater when the temperature of the sensor element is lower than the upper limit temperature. In this case, the predetermined detection timing may be set as a timing during stoppage of the internal combustion engine, and during the power control.

Further, in the present invention, the predetermined detection timing may be set as a plurality of different timings. In this case, the correction means may correct a ratio of a change to the resistance of the heater, of the temperature of the sensor element that is estimated by the second means in accordance with a ratio of a change of the first element temperature among the plurality of predetermined detection timings.

Further, in the present invention, the control device for an exhaust gas sensor may further include means for determining the exhaust gas sensor as abnormal when the difference between the first element temperature and the second element temperature exceeds a reference value.

Further, in the present invention, the control device for an exhaust gas sensor may be a control device that controls two exhaust gas sensors that are a first exhaust gas sensor installed upstream of a catalyst in the exhaust channel, and a second exhaust gas sensor that is installed downstream of the catalyst. In this case, the control device for an exhaust gas sensor may further include means for determining that the first exhaust gas sensor and/or the second exhaust gas sensor are/is abnormal, when a difference between a temperature of a sensor element of the first exhaust gas sensor that is estimated by the second means, and a temperature of a sensor element of the second exhaust gas sensor that is estimated by the second means exceeds a reference value.

Further, in the present invention, the exhaust gas sensor may be an NOx sensor for detecting an NOx amount in exhaust gas in the exhaust channel.

Advantageous Effects of Invention

According to the present invention, the temperatures of the sensor element are estimated in accordance with the impedance of the solid electrolyte and the resistance of the heater respectively, and based on the difference between the temperature of the sensor element according to the impedance and the temperature of the sensor element according to the heater resistance, the temperature of the sensor element that is detected in accordance with the heater resistance is corrected. Accordingly, even when a change arises in the resistance of the heater due to secular deterioration or the like, the change can be corrected, and precision of the temperature detection of the sensor element according to the heater resistance can be enhanced.

Further, in particular, the relation of the impedance and the temperature of the sensor element is stabilized in the case of a high temperature to some extent, and therefore, in the region at a high temperature, precision of temperature detection of the sensor element according to the impedance is high. In this regard, if the temperature of the sensor element according to the heater resistance is corrected in accordance with the first element temperature and the second element temperature that are detected when the temperature of the sensor element is higher than the reference temperature, the temperature of the sensor element according to the heater resistance can be corrected more accurately. Accordingly, the precision of temperature detection based on the heater resistance can be enhanced.

Further, for example, during fuel cut of the internal combustion engine and during idle stop, the exhaust gas temperature is low. Accordingly, if the predetermined detection timings for detecting the impedance and the heater resistance for estimation of the first and the second element temperatures for correction are set to be during a fuel cut operation of the internal combustion engine and during idle stop, the difference between the first element temperature and the second element temperature can be clearly detected. Accordingly, more accurate correction can be performed.

Further, when the addition amount of the aqueous urea solution from the aqueous urea solution adding valve of the urea SCR system is small, the amount of NOx that is discharged becomes small. Accordingly, if the predetermined detection timing is set at the time when the aqueous urea solution addition amount is smaller than the reference amount, an influence on other control by the control of detecting the first and the second element temperatures to correct the sensor element temperature of the NOx sensor, that is an exhaust gas sensor, can be restrained to be small.

Further, if the upper limit temperature that is the upper limit value of the temperature of the sensor element is set in accordance with the outside air temperature or the exhaust gas temperature, and the power supply to the heater is controlled stepwise when the temperature of the sensor element is lower than the upper limit temperature during stoppage of an operation of the internal combustion engine, temperature correction of the sensor element can be performed while condensed water in the exhaust channel is avoided, for example.

DESCRIPTION OF EMBODIMENTS

Hereinafter, embodiments of the present invention will be described with reference to the drawings. Note that in the respective drawings, the same or equivalent parts will be assigned with the same reference signs, and explanation thereof will be simplified or omitted.

Embodiment 1

Figure 1:
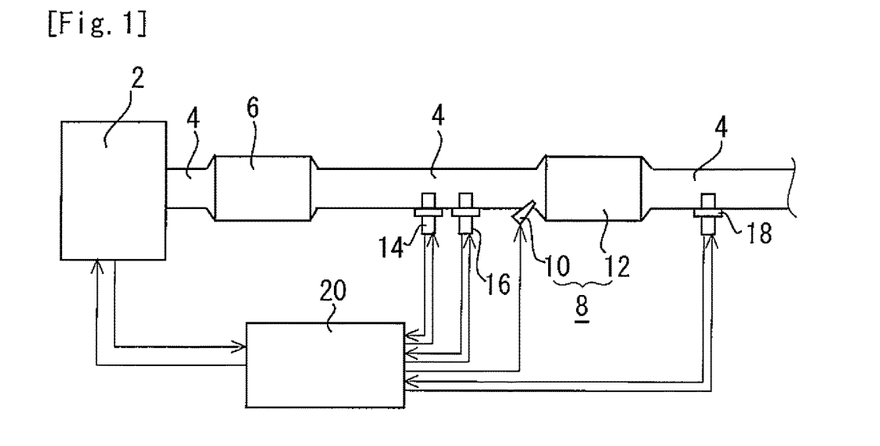
FIG. 1 is a view for explaining an entire configuration of a system of embodiment 1 of the invention.

FIG. 1 is a view for explaining an entire configuration of a system of embodiment 1 of the invention. The system shown in FIG. 1 is used by being loaded on a vehicle. In the system shown in FIG. 1, in an exhaust channel 4 of an internal combustion engine 2, a DPF (Diesel Particulate Filter) 6 that is a filter for collecting particulates is installed. Though not illustrated, in the DPF 6, an oxidation catalyst is combined and disposed. The DPF 6 is a filter that collects particulate matter (PM) contained in exhaust gas.

Downstream of the DPF 6 in the exhaust channel 4, a urea SCR system 8 (hereinafter, also called "an SCR system") is disposed. The SCR system 8 has a urea injection valve 10 and a selectively reducing NOx catalyst 12. The urea injection valve 10 injects an aqueous urea solution into the exhaust channel 4 in an upstream side of the NOx catalyst 12. The NOx catalyst 12 reduces NOx in exhaust gas to purify the exhaust gas with ammonium generated from an aqueous urea solution as a reducing agent.

Downstream of the DPF 6 and upstream of the NOx catalyst 12 in the exhaust channel 4, an NOx sensor 14 (a first exhaust gas sensor) and an air-fuel ratio sensor 16 are installed. An NOx sensor 18 (a second exhaust gas sensor) is disposed downstream of the NOx catalyst 12.

The system includes a control device 20. Various sensors of the internal combustion engine 2 besides the NOx sensor 14, the air-fuel ratio sensor 16 and the NOx sensor 18 are connected to an input side of the control device 20. Further, the aqueous urea solution injection valve 10 of the internal combustion engine 2 and other various actuators are connected to an output side of the control device 20. The control device 20 executes various kinds of control relating to an operation of the internal combustion engine 2 by executing a predetermined program based on input information from various sensors and operating various actuators and the like.

Figure 2:
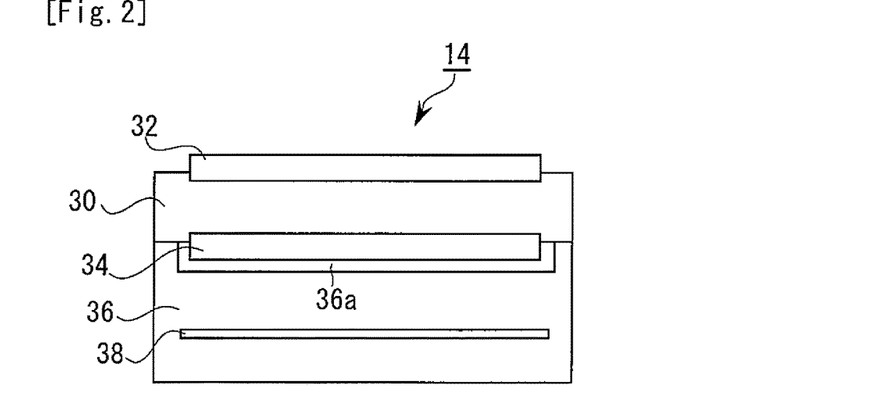
FIG. 2 is a schematic view for explaining a configuration of a sensor element of the NOx sensor of the present embodiment 1.

FIG. 2 is a schematic view for explaining a configuration of a sensor element of the NOx sensor 14 of the present embodiment 1. Note that the NOx sensor 14 will be described by being cited as an example, and the NOx sensor 18 at a downstream side of the NOx catalyst 12 is also a sensor having a similar configuration.

The NOx sensor 14 is a one-cell type sensor. More specifically, as shown in FIG. 2, the sensor element of the NOx sensor 14 includes a solid electrolyte 30. At both sides with the solid electrolyte 30 therebetween, a pair of electrodes that are composed of a detection electrode 32 and a reference electrode 34 are disposed. An insulating substrate 36 having a predetermined concave portion 36a is disposed at a surface side where a reference electrode 34 side is disposed, of the solid electrolyte 30. The reference electrode 34 is disposed in a space that is formed by the concave portion 36a of the insulating substrate 36 and the solid electrolyte 30. The detection electrode 32 is configured to be in contact with exhaust gas, and the reference electrode 34 is configured to be in contact with atmosphere that is introduced into the space where the reference electrode 34 is disposed. Further, a heater 38 is formed in the insulating substrate 36.

A configuration is such that a predetermined voltage is applied to between the detection electrode 32 and the reference electrode 34 that are the pair of electrodes via an electric circuit or the like for NOx amount detection, and a predetermined alternating voltage (alternating current voltage) for element temperature detection is applied to between the detection electrode 32 and the reference electrode 34. Further, a predetermined voltage is applied to the heater 38 via an electric circuit or the like.

In the present embodiment, control that is executed by the control device 20 includes control that detects an NOx amount contained in the exhaust gas upstream of the SCR system 8 in accordance with an output signal of the NOx sensor 14. At a time of detection of the NOx amount, a predetermined voltage is applied to between the detection electrode 32 and the reference electrode 34. By application of the voltage, NOx on the detection electrode 32 is decomposed, and a current flows into the solid electrolyte 30. The control device 20 estimates the NOx amount in the exhaust gas by detecting the current. The control device 20 performs control or the like of the injection amount of the aqueous urea solution from the urea injection valve 10, for example, in accordance with the estimated NOx amount.

Further, the control device 20 controls a temperature of the sensor element (hereinafter, also called "an element temperature") of the NOx sensor 14 to an appropriate temperature so that the NOx sensor 14 issues a correct output corresponding to the NOx amount.

More specifically, the control device 20 estimates the element temperature, controls the application voltage to the heater 38 based on the estimated element temperature, and thereby controls the element temperature. The element temperatures are estimated from resistance of the heater 38, and impedance of the solid electrolyte 30, respectively. Note that in the following embodiments, the element temperature that is estimated from the impedance will be also called "an element temperature Ti", and the element temperature that is estimated from the resistance of the heater 38 will be also called "an element temperature Tr" for convenience.

Figure 3:
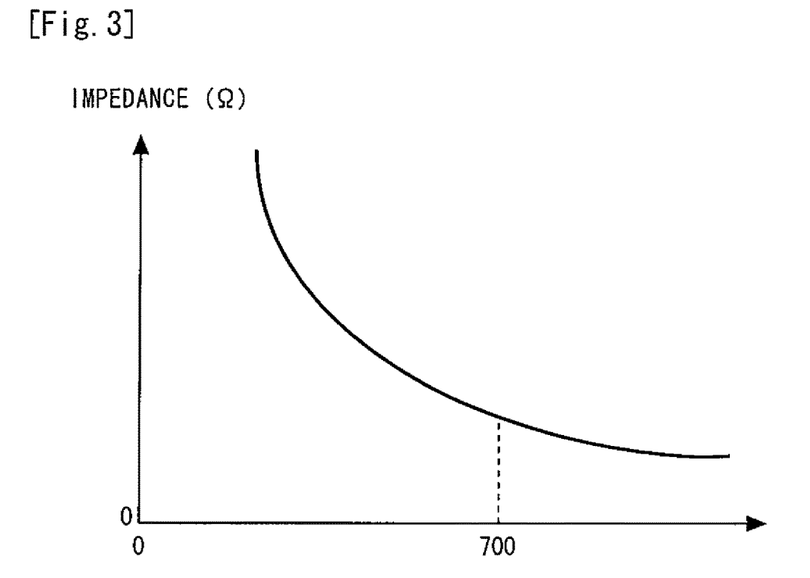
FIG. 3 is a diagram for explaining a relation of the impedance of the solid electrolyte and the element temperature Ti in the present embodiment 1.

First, estimation of the element temperature Ti based on the impedance of the solid electrolyte 30 will be described. FIG. 3 is a diagram for explaining a relation of the impedance of the solid electrolyte 30 and the element temperature Ti in the present embodiment 1. In FIG. 3, the axis of abscissa represents the element temperature Ti, and the axis of ordinates represents the impedance of the solid electrolyte 30.

At a time of impedance detection, an alternating voltage (alternating current voltage) for impedance detection is applied to between the detection electrode 32 and the reference electrode 34. As shown in FIG. 3, the impedance of the solid electrolyte 30 that is detected has a constant correlation with the element temperature. More specifically, the impedance of the solid electrolyte 30 is related to the element temperature such that as the element temperature increases, the impedance of the solid electrolyte 30 becomes smaller. Accordingly, the element temperature Ti can be estimated in accordance with the detection value of the impedance of the solid electrolyte 30. Note that an individual specific relation of the impedance of the solid electrolyte 30 and the element temperature can be obtained by an experiment or the like. The relation is stored in the control device 20 in advance as a map or an arithmetic expression (hereinafter, abbreviated as "a map or the like". In actual control, the control device 20 obtains the element temperature Ti in accordance with the detected impedance, in accordance with the map or the like in which the relation of the impedance and the element temperature Ti is set.

Figure 4:
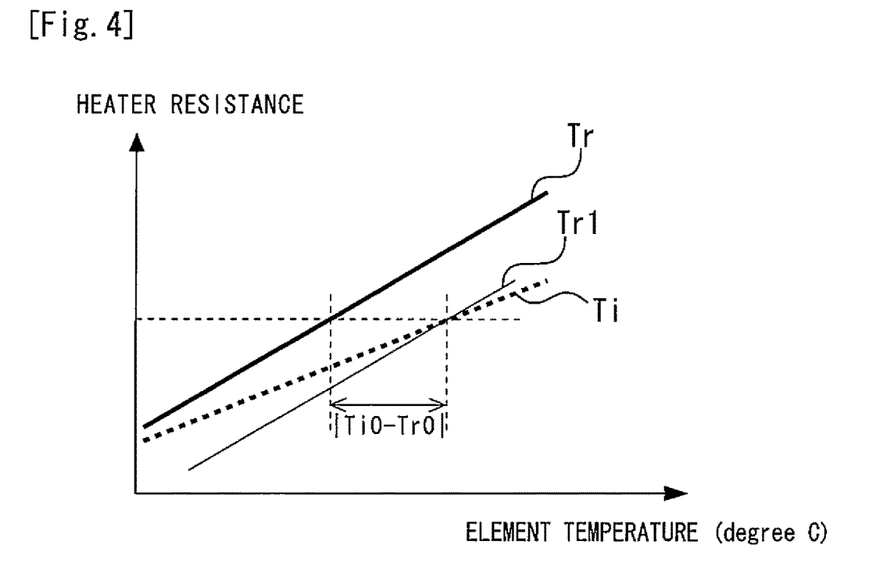
FIG. 4 is a diagram for explaining a relation of the element temperature and the resistance of the heater in the present embodiment 1.

Next, estimation of the element temperature Tr based on the resistance of the heater 38 will be described. FIG. 4 is a diagram for explaining a relation of the element temperature and the resistance of the heater 38 in the present embodiment 1. In FIG. 4, the axis of abscissa represents the element temperature, and the axis of ordinates represents the resistance value of the heater 38 (hereinafter, also called "the heater resistance R"). Further, in FIG. 4, a line Tr represents the relation of the heater resistance R and the element temperature Tr. Further, a line Ti represents the element temperature Ti detected in accordance with the impedance at a time when the heater resistance R has each value. Further, a line Tr1 represents a relation of the heater resistance R and the element temperature Tr after correction that will be described later is performed.

As shown in FIG. 4, the heater resistance R has a constant correlation with the element temperature. More specifically, the heater resistance R has such a relation that when the heater resistance R increases, the element temperature also increases proportionally. Accordingly, the element temperature can be estimated in accordance with the detection value of the heater resistance R. An individual specific relation of the heater resistance R and the element temperature Tr like this is obtained by an experiment or the like. The relation is stored in the control device 20 as a map or the like. In actual control, the control device 20 obtains the element temperature Tr in accordance with the heater resistance R, in accordance with the map or the like in which the relation of the heater resistance R and the element temperature is set.

Incidentally, when the sensor element is in a range higher than 400° C. to 500° C., for example, the impedance and the element temperature Ti described above stably show a correlation. However, when the sensor element is in a temperature region lower than 300° C., for example, variation of the correlation tends to be large. Therefore, when the sensor element is in a low temperature region, deviation easily arises in the element temperature Ti that is detected in accordance with the impedance.

Meanwhile, the heater resistance R and the element temperature show a stable correlation even in the case of being in a low temperature region. Namely, even when the sensor element is in a low temperature region, the element temperature Tr can be detected relatively accurately according to the heater resistance R.

However, since the heater 38 is formed from a material containing a metal such as platinum, change sometimes occurs to a thickness and a length of the heater 38 due to secular deterioration and the like. If the thickness and the length of the heater 38 changes, change occurs to the heater resistance R, and therefore, deviation arises in the relation of the heater resistance R and the element temperature Tr. As a result, deviation occurs between the element temperature Tr that is obtained in accordance with the heater resistance R, and the element temperature Ti that is obtained in accordance with the impedance, as shown in FIG. 4.

From the above, in the present embodiment 1, as the estimated temperatures of the sensor element, the two element temperatures that are the element temperature Ti according to the impedance, and the element temperature Tr according to the heater resistance R are compared, and thereby, abnormality of the exhaust gas sensor is detected, or the element temperature is obtained.

More specifically, the impedance of the solid electrolyte 30 and heater resistance R0 are detected at a certain timing (a detection timing) in a temperature region higher than a reference temperature that is a temperature at which the relation of the impedance and the element temperature Ti is stabilized. Note that in this case, the reference temperature is a temperature at which the impedance and the element temperature Ti show a stable correlation. The reference temperature is specifically 300° C. or higher, more preferably 400° C. to 500° C., or a temperature not lower than 400° C. to 500° C. However, the reference temperature is not limited to these temperatures and differs in accordance with the material and the like of the solid electrolyte 30, and therefore, the temperature is properly set by an experiment or the like individually and specifically.

After the impedance and the heater resistance R0 are detected, a first element temperature Ti0 corresponding to the impedance, and a second element temperature Tr0 corresponding to the heater resistance R0 are calculated. When a deviation |Ti0−Tr0| between the first element temperature Ti0 and the second element temperature Tr0 that are calculated is not within a correctable allowable range, abnormality is considered to occur to either of mechanisms that detect the element temperatures Ti and Tr. In this case, it is determined that abnormality is present in the NOx sensor 14. Here, as the reference for determination of whether or not the deviation is in an allowable range, a first reference value X1 that is a value in the vicinity of a lower limit value of the allowable range is set. The first reference value X1 is individually set in accordance of precision or the like of the temperature control that is required, and is stored in the control device 20 in advance.

Meanwhile, when a deviation occurs between the first element temperature Ti0 and the second element temperature Tr0, but is within the allowable range (range smaller than the first reference value X), the relation of the heater resistance R and the element temperature Tr is corrected in accordance with the deviation |Ti0−Tr0|. More specifically, for example, with the deviation |Ti0−Tr0| as an offset correction value, offset correction of the element temperature Tr with respect to the heater resistance R is performed. Namely, as shown by the line Tr1 of FIG. 4, the relation of the second element temperature Tr and the heater resistance R is corrected so that an amount of the deviation |Ti0−Tr0| is uniformly added to the element temperature Tr.

As described above, the impedance and the heater resistance R are detected in the temperature region higher than the reference temperature, and therefore, it is predicted that the relation of the impedance and the element temperature Ti is in a stable state, and the first element temperature Ti0 is close to the actual element temperature. Accordingly, the relation of the heater resistance R and the element temperature Tr is corrected based on the offset correction value according to the first element temperature Ti0, and thereby the relation of the heater resistance R and the element temperature Tr can be corrected correctly.

Note that as a reference for determination of whether or not such a deviation occurs to between both the element temperatures Ti0 and Tr0 that correction is needed in the relation of the element temperature Tr and the heater resistance R, a second reference value X2 is set. The second reference value X2 is individually set in accordance with precision or the like of the temperature control that is required, and is stored in the control device 20, in advance. When the deviation |Ti0−Tr0| is smaller than the first reference value, but is larger than the second reference value X2, offset correction of the relation of the heater resistance R and the element temperature Tr is performed as described above.

When the deviation |Ti0−Tr0| is the second reference value X2 or smaller, it is conceivable that no deviation is present between the first and the second element temperatures Ti0 and Tr0, and the element temperature Ti and the element temperature Tr can be both detected correctly. Accordingly, correction of the element temperatures is not especially performed, and the NOx sensor 14 is determined as normal.

Figure 5:
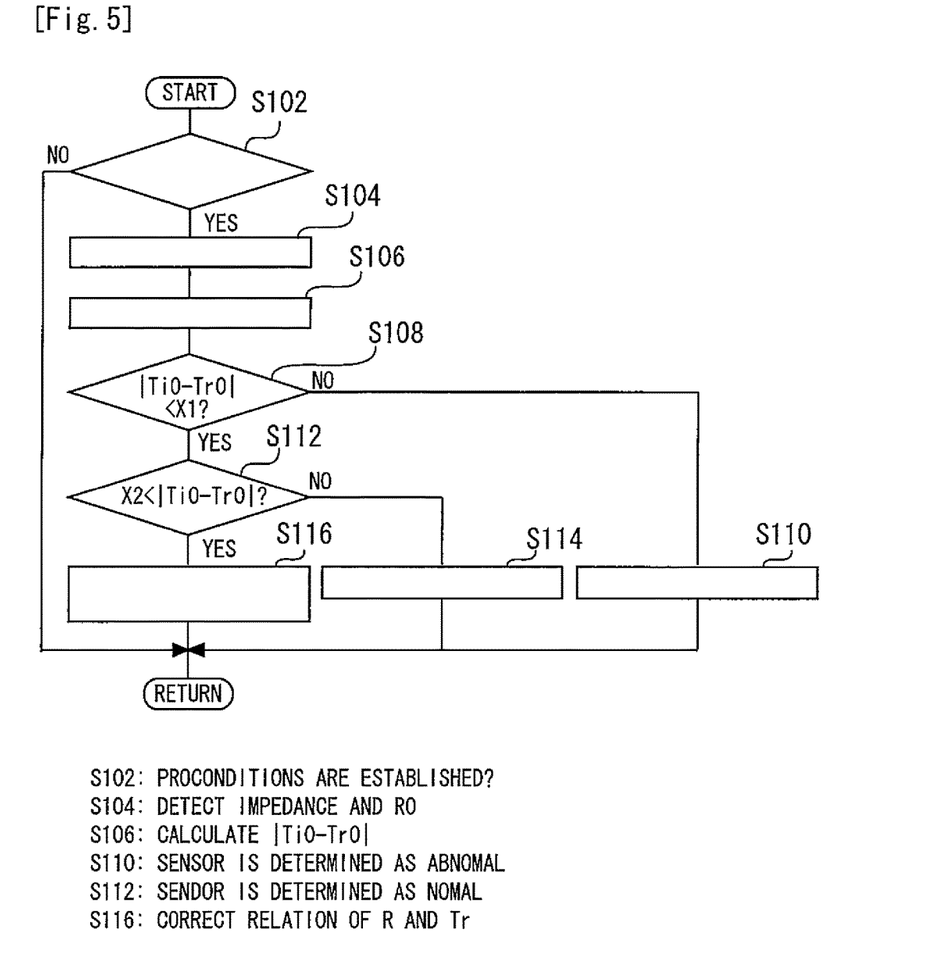
FIG. 5 is a flowchart for explaining a routine of control that is executed by the control device in the embodiment of the present invention.

FIG. 5 is a flowchart for explaining a routine of control that is executed by the control device 20 in the embodiment of the present invention. The routine in FIG. 5 is the routine that is repeatedly executed at constant periods during operation of the internal combustion engine 2.

When the routine in FIG. 5 is started, it is firstly determined whether or not preconditions are established (S102). The preconditions are conditions that are necessary to execute abnormality determination and element temperature correction of the NOx sensor 14 stably, and are stored in the control device 20 in advance. For example, the preconditions are that the internal combustion engine 2 is under operation after completion of warming up, whether or not the present element temperature Ti or the element temperature Tr is higher than the reference temperature, and the like. When establishment of the preconditions is not recognized in step S102, the processing of this time is temporarily finished.

Meanwhile, when establishment of the preconditions is recognized in step S102, the heater resistance R0 and the impedance of the solid electrolyte 30 are detected next (S104). Detection timings of the heater resistance R0 and the impedance are simultaneous with each other, or when a response delay arises in either one of them, the delay amount is taken into consideration, and the heater resistance R0 and the impedance are detected by the control device 20 at predetermined timings that are considered to be practically the same.

Next, the first element temperature Ti0 and the second element temperature Tr0 are respectively calculated, and the deviation |Ti0−Tr0| between both of them is calculated (S106). More specifically, the first element temperature Ti0 is calculated in accordance with the impedance of the solid electrolyte 30 that is detected in step S104. Further, the second element temperature Tr0 is calculated in accordance with the heater resistance R0. From the first element temperature Ti0 and the second element temperature Tr0 that are calculated, the deviation |Ti0−Tr0| of both the element temperatures is calculated.

Next, it is determined whether or not the deviation |Ti0−Tr0| is smaller than the first reference value X1 (S108). As described above, the first reference value X1 is the reference value for determination that is stored in the control device 20 in advance.

When establishment of |Ti0−Tr0|<X1 is not recognized in step S108, the deviation between the first element temperature Ti0 and the second element temperature Tr0 is considered to be a deviation that is too large to be corrected. Accordingly, the NOx sensor 14 is determined as abnormal (S110). In this case, processing at the abnormal time that is set in another control program such as lighting a warning lamp or the like is executed. After the abnormality determination in step S110, the processing of this time is finished.

Meanwhile, when establishment of |Ti0−Tr0|<X1 is recognized in step S108, it is determined whether or not the deviation |Ti0−Tr0| is larger than the second reference value X2 next (S112). As described above, the second reference value X2 is the reference value for determination that is stored in the control device 20 in advance.

When establishment of |Ti0−Tr0|>X2 is not recognized in step S112, the NOx sensor 14 is determined as normal (S114). Namely, when the deviation |Ti0−Tr0| is the second reference value X2 or less, it is determined that a deviation does not arise to such an extent that correction is required, in the first and the second element temperatures Ti0 and Tr0. Accordingly, processing of temperature correction or the like is not especially performed thereafter, and the processing of this time is temporarily finished.

Meanwhile, when establishment of |Ti0−Tr0|>X2 is recognized in step S112, the relation of the heater resistance R and the element temperature Tr is corrected based on the deviation |Ti0−Tr0| that is calculated in step S106 (S116). Thereafter, the processing of this time is finished.

As described above, according to the present embodiment 1, the element temperature Tr that is calculated in accordance with the heater resistance R is corrected based on a correction value obtained in accordance with the first element temperature Ti0 at the time of the element temperature being in a temperature region that is high to some extent. Thereby, even when some deterioration is recognized in the heater 38, the relation of the element temperature Tr and the heater resistance R is corrected by being adapted to a state in which the heater 38 is deteriorated. Accordingly, for example, in a low temperature region in which the temperature cannot be correctly detected with impedance, the element temperature can be estimated more correctly based on the heater resistance R.

Further, according to the present embodiment 1, when the deviation |Ti0−Tr0| is the second reference value X1 or more, it is determined that the deviation between the element temperature Ti and the element temperature Tr is too large to be corrected, and it is determined that the NOx sensor 14 is abnormal. Accordingly, detection of an erroneous temperature by the deteriorated NOx sensor 14, and error determination can be effectively prevented.

Note that in the present embodiment 1, the configuration of the NOx sensor 14 is explained in FIG. 2. However, in the present invention, the NOx sensor 14 is not limited to this configuration, and may be of another configuration if only the NOx sensor 14 includes a pair of electrodes with a solid electrolyte therebetween and a heater. This also applies to the following embodiments.

Further, in the present embodiment 1, the case of having the NOx sensors 14 and 18 respectively upstream and downstream of the SCR system 8, and having the air-fuel ratio sensor 16 upstream of the SCR system 8 is described. However, in the present invention, the installation positions of the NOx sensors and the air-fuel ratio sensor 16 are not limited to them. Further, in the present invention, temperature correction of the NOx sensor 14 is described. However, the invention is not limited to this, and similar abnormality determination and temperature correction can be also applied to the NOx sensor 18, the air-fuel ratio sensor 16, and besides them, other NOx sensors and the like each of a type having a solid electrolyte and a pair of electrodes at both sides thereof. This also applies to the following embodiments.

Further, in the present embodiment 1, the case in which the relation of the heater resistance R and the element temperature Tr is corrected only when the deviation |Ti0−Tr0| is larger than the second reference value X2. However, the present invention is not limited to the control device that performs determination like this, and the relation of the heater resistance R and the element temperature Tr may be corrected irrespective of the extent of the deviation |Ti0−Tr0|. This also applies to the following embodiments.

Further, when the air-fuel ratio sensor 16 is disposed in the vicinity of the NOx sensor 14 as in the present embodiment 1, the element temperatures of the NOx sensor 14 and the air-fuel ratio sensor 16 are detected at the same timing, the element temperatures are compared, and when the difference between the element temperatures of both of them is as large as or larger than the reference, abnormality determination of the NOx sensor 14 or the air-fuel ratio sensor 16 can be performed. In this case, abnormality determination based on the first and the second element temperatures Ti0 and Tr0 that is described above is performed, and precision of determination may be enhanced, or abnormality determination based on the first and the second element temperatures Ti0 and Tr0 does not have to be performed. Further, the respective element temperatures of the NOx sensor 14 and the air-fuel ratio sensor 16 for use in comparison may be the element temperatures according to the impedance or may be the element temperatures according to the heater resistance. Further, for example, as described in the present embodiment 1, the element temperature that is the result of correcting the element temperature Tr according to the heater resistance R in accordance with the first element temperature Ti0 is obtained with respect to each of the NOx sensor 14 and the air-fuel ratio sensor 16, and the element temperatures after correction may be used. By comparing the element temperatures Tr corrected like this, abnormality determination of the exhaust gas sensor can be performed more reliably. This also applies to the following embodiments.

Further, abnormality determination of the sensors can be also performed based on the element temperatures of the two sensors disposed with the SCR system 8 therebetween, like the relation of the NOx sensor 14 and the NOx sensor 18, for example, without being limited to the case in which a plurality of sensors are disclosed near to one another. In this case, the element temperatures of the NOx sensor 14 and the NOx sensor 18 are respectively compared similarly. At this time, the temperature reduction amount of the exhaust gas from the NOx sensor 14 to the NOx sensor 18 is estimated, and with the temperature reduction amount taken into consideration, comparison of the element temperatures is performed. Thereby, even when the sensors of the same type are located at the relatively distant positions, abnormality determination can be performed by comparison of the element temperatures. This also applies to the following embodiments.

Further, in the present embodiment 1, the case of performing offset correction of the relation of the heater resistance R and the element temperature Tr by uniformly adding the deviation |Ti0−Tr0| is described. Here, it is conceivable that when the length and the width of the heater resistance R change due to deterioration of the heater 38, offset deviation arises in the relation of the heater resistance R and the temperature. Accordingly, in the relation of the heater resistance R and the temperature Tr, offset correction that uniformly adds the offset correction value based on the deviation |Ti0−Tr0| is effective. However, the present invention is not limited to the correction method like this, and the relation of the element temperature Tr and the heater resistance R may be corrected by using another parameter (for example, a ratio or the like) relating to the difference of the first element temperature Ti0 and the second element temperature Tr0. This also applies to the following embodiments.

Further, in the present embodiment 1, the case of correcting the relation of the element temperature Tr and the heater resistance R is described. However, the present invention is not limited to this, and correction may be made by other methods. For example, after the element temperature Tr is calculated based on the relation of the second element temperature Tr and the heater resistance R that is stored in the control device 20, the element temperature Tr may be corrected by the correction value calculated based on the difference of the first and the second element temperatures Ti0 and Tr0, or by obtaining the correction value for the heater resistance R that is detected from the difference between the first element temperature Ti0 and the second element temperature Tr, the detection value of the heater resistance R may be corrected. This also applies to the following embodiments.

Further, in the present embodiment 1, the case of using the corrected element temperature Tr in the temperature control of the sensor element is described. However, since the element temperature changes in tandem with the exhaust gas temperature to some extent, the exhaust gas temperature can be estimated correctly to some extent by correctly detecting the element temperature. Accordingly, the NOx sensors 14 and 18 and the air-fuel ratio sensor 16 in the present embodiment 1 can be used as temperature sensors that detect the temperature of the exhaust gas. Further, by using the element temperature Tr based on the heater resistance R, that is corrected here, the exhaust gas temperature can be detected more accurately. This also applies to the following embodiments.

Embodiment 2

Configurations of a system and an NOx sensor of second embodiment are the same as those shown in FIG. 1 and FIG. 2. Further, in the system of embodiment 2, control of temperature correction is performed by correcting the relation of the element temperature Tr and the heater resistance R, but a method of the correction differs from that of the system of embodiment 1.

Figure 6:
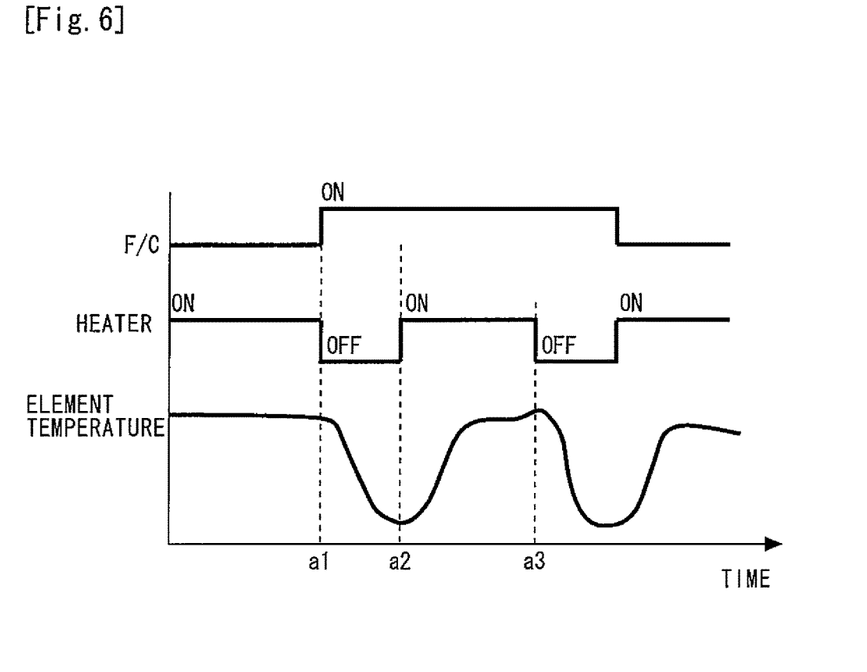
FIG. 6 is a timing chart for explaining control in a case of performing temperature correction in embodiment 2 of the present invention.

FIG. 6 is a timing chart for explaining control in a case of performing temperature correction in embodiment 2 of the present invention. As shown in FIG. 6, in the system of the present embodiment 2, detection timings of impedance and the heater resistance R for calculation of a correction value are set during a fuel cut operation (described as "F/C" in the drawing). This is because a state in which a deviation that occurs between the first element temperature Ti0 and the second element temperature Tr0 is easily detected clearly is brought about since the exhaust temperature is low during a fuel cut operation. Further, an NOx exhaust amount is small during a fuel cut operation. Accordingly, even if the NOx amount detection by the NOx sensor 14 is stopped for calculation of the correction value of the NOx sensor 14, an influence given to the system thereby is small. Accordingly, control of calculation of the correction value in the present embodiment 2 is executed during a fuel cut operation.

Further, in the system of the present embodiment 2, in order to calculate a correction value, ON/OFF control of the heater 38 that alternately repeats a state in which a voltage is applied to the heater 38 and a state in which voltage application is stopped, is performed during a fuel cut operation. The impedance and the heater resistance R are monitored during the ON/OFF control of the heater 38, whereby changes of the first element temperature Ti0 and the second element temperature Tr0 are respectively obtained, and a correction value is detected based on the difference of both of them.

More specifically, as shown in the timing chart of FIG. 6, at a time point a1, a fuel cut operation is started, and the heater 38 is turned off at the same time. After the heater 38 is turned off, an element temperature (an actual temperature) gradually reduces. Thereafter, at a time point a2, the heater 38 is turned on again. When the heater 38 is turned on, the element temperature (the actual temperature) starts to increase again. Further, at a time point a3, the heater 38 is turned off again. The element temperature (the actual temperature) starts to reduce.

As described above, during the fuel cut operation, ON/OFF control of the heater 38 is performed, whereby the element temperature is forcefully varied. In this state, the impedance and the heater resistance R are continuously detected, whereby the change of the first element temperature Ti0 and the change of the second element temperature Tr0 can be continuously detected, and the first element temperature Ti0 and the second element temperature Tr0 at a plurality of points can be obtained.

In the present embodiment 2, differences between the first element temperatures Ti0 and the second element temperatures Tr0 at the plurality of points are averaged, and thereby an offset correction value Y0 with which the relation of the heater resistance R and the element temperature Tr is uniformly corrected is calculated. Thereby, offset correction of the relation of the heater resistance R and the element temperature Tr is performed.

Further, in addition to the offset correction value Y0, gain correction that corrects a ratio of the change of the element temperature Tr to the heater resistance R (a gradient of the line Tr in FIG. 4) is performed. More specifically, from the first element temperatures Ti0 and the second temperatures Tr0 that are monitored, respective average values of ratios of the changes are obtained, and the ratio of the change of the first element temperature Ti0 to the ratio of the change of the second element temperature Tr0 is calculated. This is set as a gain correction value Z0, and the ratio of the change of the element temperature Tr to the heater resistance R (the gradient of the line Tr of FIG. 4) is corrected, whereby gain correction of the relation of the heater resistance R and the element temperature Tr is performed.

For example, when oxidation or the like arises in the heater 38, a change arises in the composition of the material that composes the heater 38. In such a case, a deviation occurs to the ratio of the change of the element temperature Tr to the heater resistance R. In the present embodiment 2, such a deviation can be corrected by the gain correction.

Further, in the present embodiment 2, abnormality determination of the NOx sensor 14, and determination of whether it is in the range that requires correction are performed by using not only the offset correction value Y0 (namely, an average of the deviations |Ti0−Tr0|) but also the gain correction value Z0. More specifically, when an absolute value |Y0| of the offset correction value Y0 that is calculated as described above is larger than a first offset reference value Y1, and an absolute value Z0 of the gain correction value Z0 is a first gain reference value Z1 or larger, it is determined that the NOx sensor 14 is abnormal. Here, the first offset reference value Y1 and the first gain reference value Z1 are respectively reference values for determination of whether or not the deviation of the element temperature Tr and the element temperature Ti is within an allowable range, are individually set in accordance with the required precision or the like of the temperature control, and are stored in the control device 20 in advance.

Further, similarly, when the absolute value |Y0| of the offset correction value Y0 is smaller than the first offset correction value Y1 and is not smaller than a second offset correction value Y2, and the gain correction value Z0 is smaller than the first offset correction value Z1 and is not smaller than a second gain correction value Z2, the deviation that arises in the element temperature Tr is determined as within the allowable range, and the relation of the heater resistance R and the element temperature Tr is corrected as described above. Meanwhile, when the absolute value |Y0| of the offset correction value Y0 is smaller than the second offset correction value Y2, and the gain correction value Z0 is smaller than the second gain correction value Z2, it is determined that a deviation does not arise in the element temperature Tr, and the NOx sensor 14 is determined as normal. Note that the second offset correction value Y2 and the second gain correction value Z2 are respectively reference values for determination of whether or not correction is necessary, are individually set in accordance with required precision of temperature control, and are stored in the control device 20 in advance.

Figure 7:
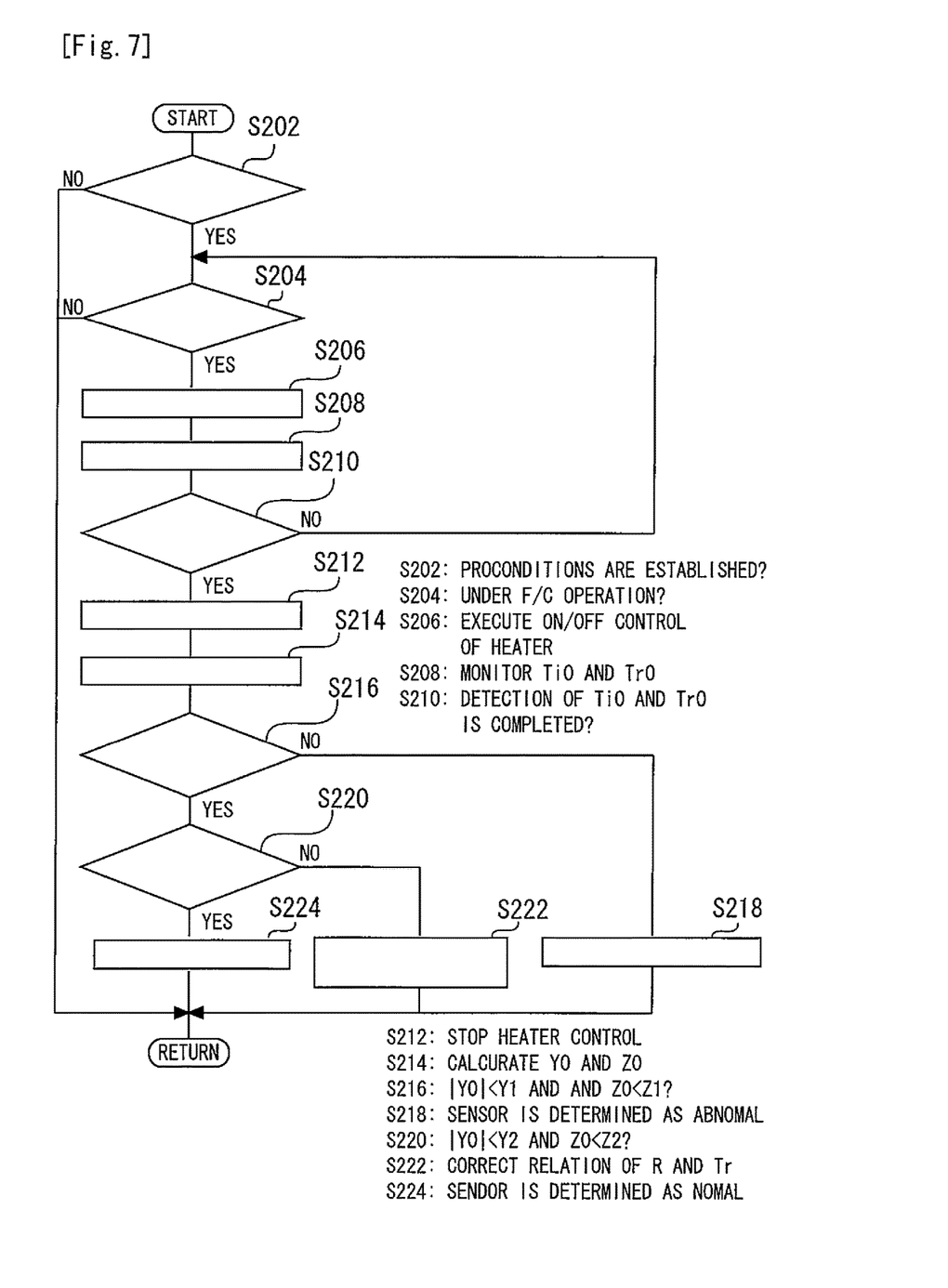
FIG. 7 is a flowchart for explaining a routine of control executed by the control device in embodiment 2 of the present invention.

FIG. 7 is a flowchart for explaining a routine of control executed by the control device 20 in embodiment 2 of the present invention. The routine of FIG. 7 is repeatedly executed at constant periods during an operation of the internal combustion engine 2. In the routine of FIG. 7, in step S202, it is determined whether or not establishment of the preconditions is recognized similarly to step S102 of FIG. 52, and when establishment is not recognized, the processing of this time is finished.

Meanwhile, when establishment of the preconditions is recognized in step S202, it is determined whether or not the internal combustion engine is under a fuel cut operation next (S204). When it is not recognized that the internal combustion engine is under a fuel cut operation in step S204, the processing of this time is finished.

Meanwhile, when it is recognized that the internal combustion engine is under a fuel cut operation in step S204, control of ON/OFF of the heater 38 is executed next (S206). Here, the state in which a voltage is applied to the heater 38 and the state in which voltage application to the heater 38 is stopped are repeated at predetermined periods.

In this state, the first element temperature Ti0 and the second element temperature Tr0 are monitored (S208). The first element temperature Ti0 is obtained in accordance with impedance, in accordance with a map or the like in which the relation of the impedance and the element temperature Ti is set. Meanwhile, the second element temperature Tr0 is obtained in accordance with the heater resistance R, in accordance with the map or the like in which the relation of the heater resistance R and the element temperature Tr is set.

Next, it is determined whether or not monitoring of the first element temperature Ti0 and the second element temperature Tr0 is completed (S210). Namely, it is determined whether or not monitoring of the first element temperature Ti0 and the second element temperature Tr0 in step S280 is performed to such an extent that is needed for calculation of the respective correction values Y0 and Z0. More specifically, it can be determined based on whether the elapsed time from start of monitoring exceeds a predetermined time period or the like, for example. When detection completion of the first and the second element temperatures Ti0 and Tr0 is not recognized in step S210, the process is returned to step S204 again, and the processing of steps S204 to S210 is executed as described above.

Meanwhile, when detection completion of the first and the second element temperatures Ti0 and Tr0 is recognized, control of ON/OFF of the heater 38 is stopped next (S212). Next, from the detected first and second element temperatures Ti and Tr, the offset correction value Y0 and the gain correction value Z0 with which the relation of the second element temperature Tr and the resistance of the heater 38 is corrected are calculated (S214). The offset correction value Y0 and the gain correction value Z0 are obtained by the predetermined processing of the control device 20.

Next, it is determined whether or not the absolute value |Y0| of the offset correction value Y0 is smaller than the first offset reference value Y1, and the gain correction value Z0 is smaller than the first gain reference value Z1 (S216). Here, the first offset reference value Y1 and the first gain reference value Z1 are the values that are stored in the control device 20 in advance.

When establishment of |Y0|<Y1 and Z0<Z1 is not recognized in step S216, it is determined that the NOx sensor 14 has abnormality (S218), and after predetermined control of lighting a warning lamp or the like is executed, the processing of this time is finished.

Meanwhile, when establishment of |Y0|<Y1 and Z0<Z1 is recognized in step S216, it is determined whether or not the absolute value |Y0| of the offset reference value Y0 is smaller than the second offset reference value Y2, and the gain correction value Z0 is smaller than the second gain reference value Z2 (S220). The second offset reference value Y2 and the second gain reference value Z2 are the values that are stored in the control device 20 in advance.

When establishment of |Y0|<Y2, and Z0<Z2 is not recognized in step S220, the relation of the heater resistance R and the second element temperature Tr is corrected by the offset correction value Y0 and the gain correction value Z0 (S222). Thereafter, the processing of this time is finished.

Meanwhile, when establishment of |Y0|<Y2, and Z0<Z2 is recognized in step S218, a deviation is not present between the second element temperature Tr0 and the first element temperature Ti0, or the deviation is extremely small, and the NOx sensor 14 is determined as normal (S224). In this case, correction or the like is not especially required, and therefore, the processing of this time is directly finished.

As described above, according to the present embodiment 2, the changes of the first element temperature Ti0 and the second element temperature Tr0 at a plurality of points are detected by changing the element temperatures by control of ON/OFF of the heater 38 during a fuel cut operation. Thereby, determination of abnormality of the NOx sensor, or correction of the temperature detection value of the sensor element can be performed with higher precision.

Note that in the present embodiment 2, the case of calculating the correction values by detecting the first and the second element temperatures Ti0 and Tr0 at the timings during a fuel cut operation is described. Since the exhaust gas temperature and the NOx concentration are low during fuel cut, control influence is restrained to be small, and the deviation of the element temperatures Ti and Tr can be detected more accurately. However, in the present invention, monitoring of the first and the second element temperatures Ti0 and Tr0 is not limited to the above timings, and may be performed in other operation states. However, the environment in which the exhaust gas temperature is low and the NOx exhaust amount is small is preferable, more specifically, the time period in which the internal combustion engine 2 is stopped in idle stop control, the case in which the amount of addition of urea in the SCR system is smaller than the reference addition amount and the like, for example, are preferable besides the timings during a fuel cut operation.

Further, in embodiment 2, the case of calculating the offset correction value Y0 and the gain correction value Z0 based on the first and the second element temperatures Ti0 and Tr0 that are monitored during ON/OFF control of the heater 38, and performing offset correction and gain correction of the relation of the heater resistance R and the element temperature Tr is described. However, in the present invention, the method for correction is not limited to this. For example, the method may be the one that obtains the first and the second element temperatures Ti0 and Tr0 in two or more detection timings during the ON/OFF control of the heater 38, and thereby calculates the offset correction value Y0 and the gain correction value Z0.

Further, the method is not limited to the one that performs both offset correction and gain correction, and may be the one that detects the first element temperature Ti0 and the second element temperature Tr0 once or a plurality of times, under the predetermined condition such as being under fuel cut, and performs any one of the offset correction and the gain correction for the relation of the heater resistance R and the element temperature Tr.

Further, in addition, the method for correction is not limited to the above, and can be any method in which the relation of the heater resistance R and the element temperature Tr is corrected by other techniques in accordance with the difference (a difference, a ratio or the like) between the first element temperature Ti0 and the second element temperature Tr0 that are detected once or a plurality of times.

Further, for example, an object to be corrected is not limited to the relation of the heater resistance R and the element temperature Tr, and the detection value of the resistance R of the heater 38 may be directly corrected, for example, and the element temperature Tr that is calculated based on the relation between the heater resistance R and the element temperature Tr may be corrected.

Embodiment 3

A system and an NOx sensor of embodiment 3 have the same configurations as the systems and the NOx sensors of FIG. 1 and FIG. 2. The system of embodiment 3 performs correction of the second element temperature Tr by the same control as in the system of embodiment 2 except for the feature of performing correction of the second element temperature Tr based on the element temperatures that are detected when the voltage that is applied to the heater 38 is changed stepwise while the internal combustion engine 2 is stopped.

Figure 8:
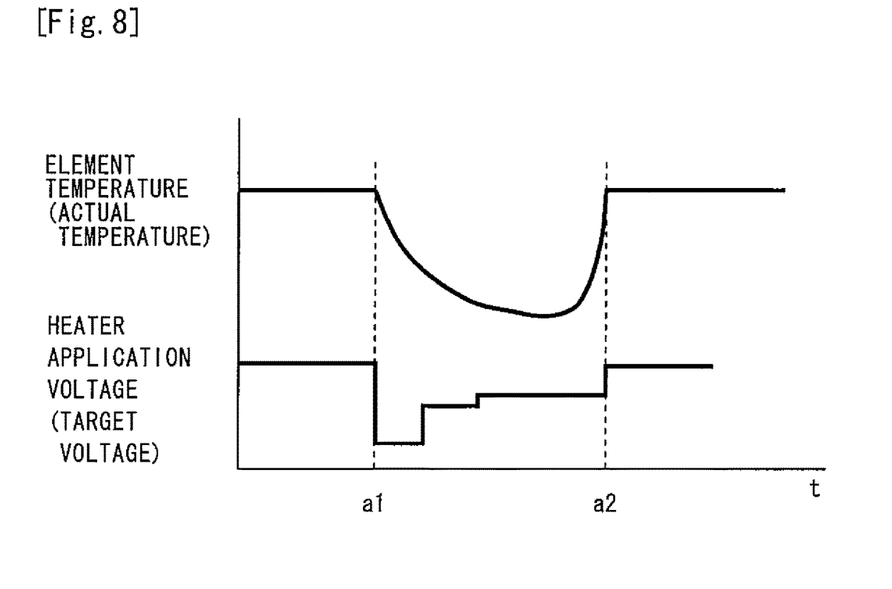
FIG. 8 is a timing chart for explaining the control in embodiment 3 of the present invention.

FIG. 8 is a timing chart for explaining the control in embodiment 3 of the present invention. The system of embodiment 3 performs control so that the application voltage to the heater 38 becomes larger stepwise from a state in which the heater 38 is turned off once at a time point a1 at which the internal combustion engine 2 is stopped. In this state, the application voltage to the heater 38 becomes small once, and therefore, an element temperature (an actual temperature) gradually reduces after stoppage of the internal combustion engine 2, and thereafter, increases.

Note that in the control of stepwise voltage application, the application voltage does not have to be increased at a constant ratio. For example, such a setting may be made that makes the increase amount small when the outside air temperature becomes high, or the like.

During the control like this, the impedance and the heater resistance R are monitored, and changes of the first and the second element temperatures Ti0 and Tr0 corresponding to them are monitored and detected. The offset correction value Y0 and the gain correction value Z0 are calculated similarly to the case of embodiment 2 in accordance with the first and the second element temperatures Ti0 and Tr0 during the control. Furthermore, abnormality of the NOx sensor 14 is determined, or output correction of the NOx sensor 14 is performed, similarly to the system of embodiment 2 in accordance with the offset correction value Y0 and the gain correction value Z0.

Further, in the control of increasing the application voltage of the present embodiment 3, a temperature at which dew condensation water is generated in the exhaust channel 4 is obtained, and voltage application is performed with this temperature as an upper limit temperature. Namely, the element temperature Ti is detected during control of voltage application, and the application voltage is increased stepwise within a range in which the element temperature Ti is lower than the upper limit temperature.

Figure 9:
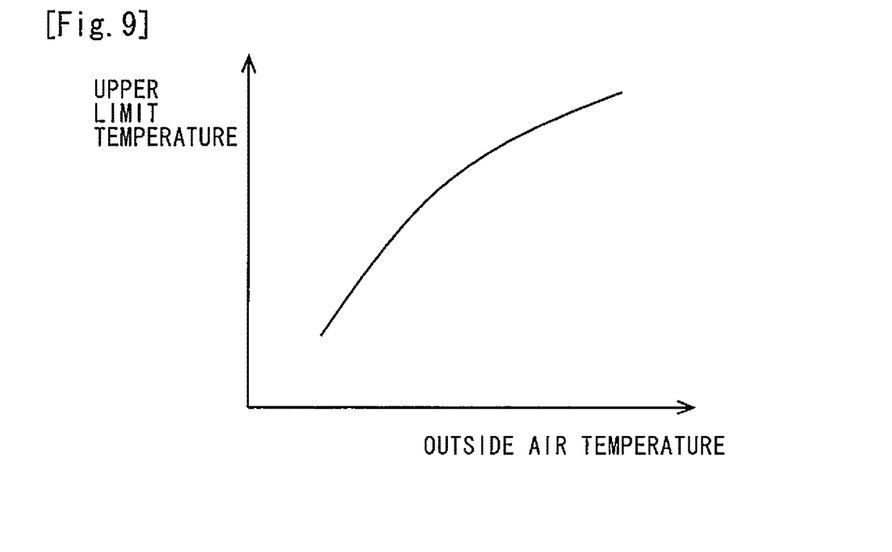
FIG. 9 is a diagram for explaining the upper limit temperature with respect to the outside air temperature that is set in embodiment 3 of the present invention.

FIG. 9 is a diagram for explaining the upper limit temperature with respect to the outside air temperature that is set in embodiment 3 of the present invention. As shown in FIG. 9, the upper limit temperature that is a temperature at which generation of dew condensation water is predicted has correlation with the outside air temperature, and as the outside air temperature becomes higher, the upper limit temperature also becomes higher. The relation as specifically shown in FIG. 9 is obtained by an experiment or the like in advance, and is stored in the control device 20 as a map or the like. The upper limit temperature is set in accordance with the outside air temperature based on the map or the like.

Figure 10:
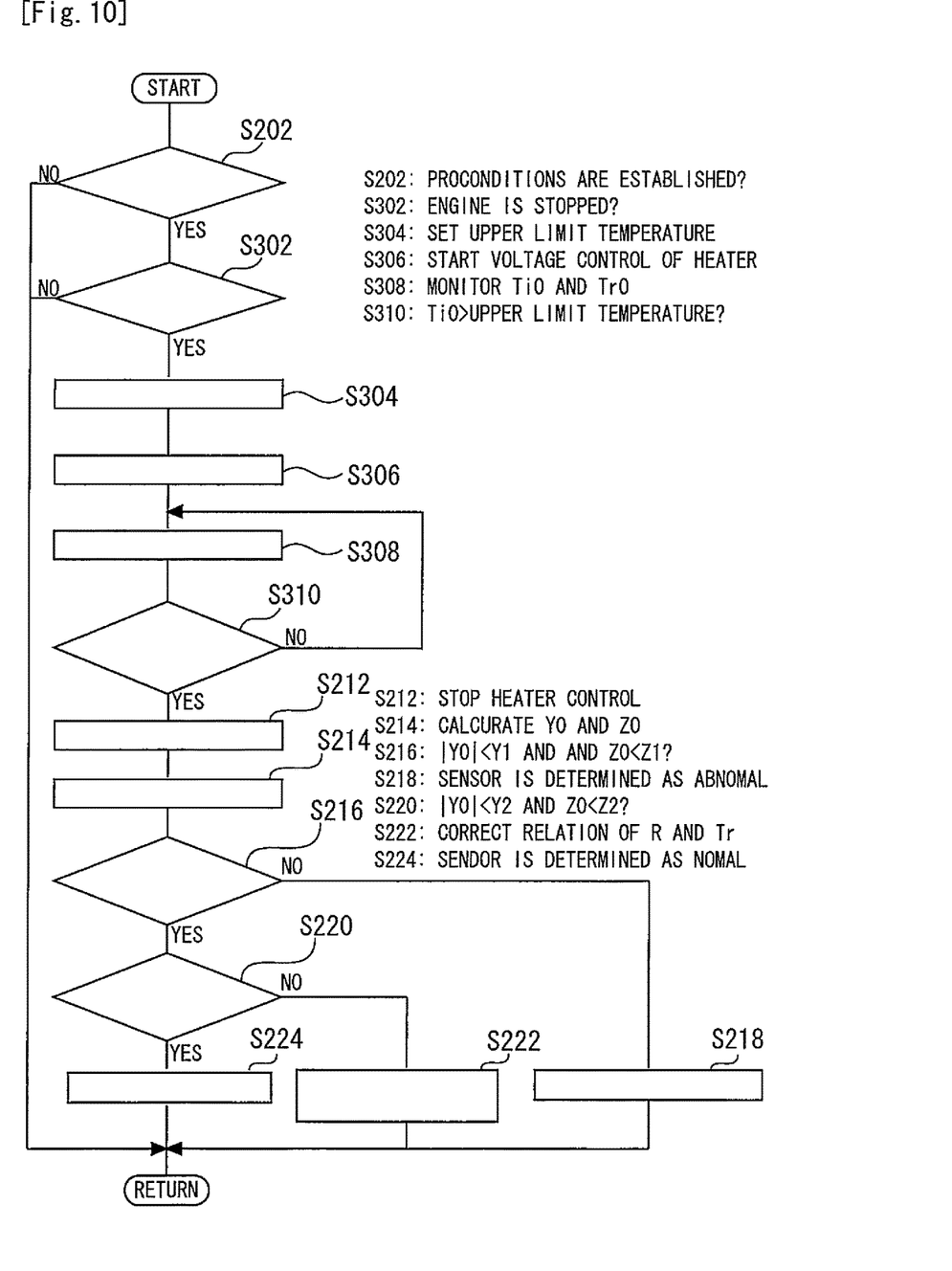
FIG. 10 is a flowchart for explaining a routine of the control that is executed by the control device in embodiment 3 of the present invention.

FIG. 10 is a flowchart for explaining a routine of the control that is executed by the control device 20 in embodiment 3 of the present invention. The routine of FIG. 10 is the same as the routine of FIG. 7 except for the feature of having processing of S302 to S310 in place of S204 to S210 after step S202 of the routine of FIG. 7, before the processing of step S212. In FIG. 10, after establishment of the predetermined preconditions that the element temperature is higher than the reference temperature and the like, for example, is recognized, it is determined whether or not the internal combustion engine 2 stops (S302). When stoppage of the internal combustion engine 2 is not recognized in step S302, the processing of this time is finished.

Meanwhile, when stoppage of the internal combustion engine 2 is recognized in step S302, the upper limit temperature in correction is set from the outside air temperature next (S304). The upper limit temperature is a temperature that does not generate dew condensation water at the time of the next start, or for restraining deterioration of the NOx sensor 14 even when dew condensation water is generated and the NOx sensor 14 is covered with the water, and the upper limit temperature according to the outside air temperature is set based on the relation of the outside air temperature and the upper limit temperature that is stored in the control device 20 in advance.

Next, voltage control to the heater 38 is started (S306). More specifically, control is performed so that the application voltage changes stepwise from the present application voltage. Further, the application voltage is adjusted in accordance with the outside air temperature.

Next, under the environment in which the application voltage to the heater 38 is controlled, the first element temperature Ti0 and the second element temperature Tr0 are monitored (S308). Namely, continuous detection timings for the impedance and the heater resistance are set to be during application voltage control, the first element temperature Ti0 is continuously detected in accordance with the impedance, and the second element temperature Tr0 is continuously detected in accordance with the heater resistance R.

Next, it is determined whether or not the present first element temperature Ti0 is higher than the upper limit temperature (S310). Here, the upper limit temperature is the temperature that is set in step S304. When establishment of the first element temperature Ti0>the upper limit temperature is not recognized in step S310, the process is returned to step S308. Namely, until establishment of the first element temperature Ti0>the upper limit temperature is recognized in step S310, monitoring of the first and the second element temperatures Ti0 and Tr0 is performed under the environment in which stepwise control of the application voltage to the heater 38 is performed.

Meanwhile, when establishment of the first element temperature Ti0>the upper limit temperature is recognized in step S310, the processing of S212 to S224 of the routine in FIG. 7 is similarly performed. Thereby, based on the first element temperature Ti0 and the second element temperature Tr0 that are monitored under the environment in which the application voltage to the heater 38 is increased stepwise, abnormality of the NOx sensor 14 is detected, or correction of the element temperature Tr is performed in accordance with necessity.

As described above, according to the present embodiment 3, the element temperature Tr can be corrected based on the first element temperature Ti0 and the second element temperature Tr0 under the environment in which generation of dew condensation water at the time of correction is restrained.

Note that in the present embodiment 3, explanation is made about setting the upper limit temperature in accordance with an outside air temperature, but the parameter for setting the upper limit temperature is not limited to the outside air temperature. For example, the upper limit temperature may be set in accordance with the cooling water and exhaust gas temperatures of the internal combustion engine 2. Further, the upper limit temperature may be set based on a plurality of parameters including an outside air temperature, the cooling water and exhaust gas temperatures.

Further, in the present embodiment 3, the case of performing control so that the element temperature gradually increases by controlling the application voltage to the heater 38 is described. However, in the present invention, the control is not limited to the one that controls the application voltage, and may be the one that controls the supply power and current to the heater 38 and the like.

When the numerals of the number, the quantity, the amount, the range and the like of each of the elements are mentioned in the above embodiments, the present invention is not limited to the mentioned numerals except for the case of being especially explicitly mentioned otherwise, and the case of being explicitly specified to be the numerals theoretically. Further, the structures, the manufacturing process steps and the like that are described in the embodiments are not always essential to the present invention except for the case of being especially explicitly mentioned otherwise, and the case of being explicitly specified to be the structures, the manufacturing processes or the like theoretically.

DESCRIPTION OF REFERENCE NUMERALS 2 internal combustion engine
4 exhaust channel
8 SCR system
10 urea injection valve
12 NOx catalyst
14 NOx sensor
16 air-fuel ratio sensor
18 NOx sensor
20 control device
30 solid electrolyte
32 detection electrode
34 reference electrode
36 insulating substrate
38 heater

The invention claimed is:

1. A control device for an exhaust gas sensor configured to control the exhaust gas sensor disposed in an exhaust channel of an internal combustion engine,
the exhaust gas sensor including:
a solid electrolyte,
a pair of electrodes disposed with the solid electrolyte therebetween, and
a heater that heats a sensor element of the exhaust gas sensor;
the control device programmed to:
estimate, as a first element temperature, a temperature of the sensor element in accordance with impedance of the solid electrolyte in the absence of resistance of the heater in a temperature range in which the temperature of the sensor element is greater than a reference temperature;
estimate, as a second element temperature, the temperature of the sensor element in accordance with resistance of the heater at least in the temperature range in which the temperature of the sensor element is less than or equal to the reference temperature; and
correct the second element temperature of the sensor element that is estimated by the control device in the temperature range in which the temperature of the sensor element is less than or equal to the reference temperature, in accordance with a difference between the first element temperature at a predetermined detection timing, and the second element temperature that is estimated at a timing corresponding to the predetermined detection timing.

2. The control device according to claim 1,
wherein the control device is programmed to estimate the second element temperature based on a relation of the resistance of the heater and the temperature of the sensor element, and
the control device is programmed to correct the relation of the resistance of the heater and the temperature of the sensor element in accordance with the difference between the first element temperature and the second element temperature.

3. The control device according to claim 1,
wherein the predetermined detection timing is a timing in a time period in which the temperature of the sensor element is higher than a reference temperature.

4. The control device according to claim 1,
wherein the predetermined detection timing is at least one from among a timing during a fuel cut operation of the internal combustion engine, a stoppage in idle stop control of the internal combustion engine, and an operation state of the internal combustion engine in which an addition amount of an aqueous urea solution from an aqueous urea solution adding valve of an urea SCR system that is installed in the exhaust channel is smaller than a reference addition amount.

5. The control device according to claim 4, further programmed to:
perform a heater ON/OFF control that alternately realizes a state in which power is supplied to the heater, and a state in which power supply is stopped,
wherein the predetermined detection timing is a timing during the heater ON/OFF control.

6. The control device according to claim 1, further programmed to:
set an upper limit temperature that is an upper limit value of the temperature of the sensor element in accordance with an outside air temperature or an exhaust gas temperature or a temperature of cooling water of the internal combustion engine, during stoppage of an operation of the internal combustion engine; and
perform power control that increases supply power to the heater stepwise when the temperature of the sensor element is lower than the upper limit temperature,
wherein the predetermined detection timing is a timing during the stoppage of the internal combustion engine, and during the power control.

7. The control device according to claim 1,
wherein the predetermined detection timing is a plurality of different timings, and
the control device programmed to correct a ratio of a change to the resistance of the heater, of the temperature of the sensor element that is estimated as the second temperature element in accordance with a ratio of a change of the first element temperature among the plurality of predetermined detection timings.

8. The control device according to claim 1, further programmed to:
determine the exhaust gas sensor as abnormal when the difference between the first element temperature and the second element temperature exceeds a reference value.

9. The control device according to claim 1, further programmed to:
control two exhaust gas sensors that are a first exhaust gas sensor installed upstream of a catalyst in the exhaust channel, and a second exhaust gas sensor that is installed downstream of the catalyst; and determine that at least one of the first gas sensor and the exhaust gas sensor is abnormal, when a difference between a temperature of a sensor element of the first exhaust gas sensor that is estimated as the second element temperature, and a temperature of a sensor element of the second exhaust gas sensor that is estimated as the second element temperature exceeds a reference value.

10. The control device according to claim 1,
wherein the exhaust gas sensor is an NOx sensor for detecting an NOx amount in exhaust gas in the exhaust channel.

* * * * *